United States Patent [19]

Robert et al.

[11] Patent Number: 4,662,731
[45] Date of Patent: May 5, 1987

[54] APPARATUS FOR EXAMINATION OF THE INNERMOST PART OF AN EYE

[75] Inventors: Yves Robert, Bernoullistrasse 10, CH-4056 Basel; Phillip Hendrickson, Basel, both of Switzerland

[73] Assignee: Yves Robert, Zurich, Switzerland

[21] Appl. No.: 651,061

[22] Filed: Sep. 14, 1984

[30] Foreign Application Priority Data

Sep. 19, 1983 [CH] Switzerland .................. 5073/83

[51] Int. Cl.$^4$ .................................................. A61B 3/10
[52] U.S. Cl. ..................................... 351/214; 351/210; 351/211; 351/221
[58] Field of Search ............... 351/205, 206, 208, 209, 351/210, 211, 214, 221; 128/633

[56] References Cited

U.S. PATENT DOCUMENTS 4,019,813 4/1977 Cornsweet et al. .................. 351/205

OTHER PUBLICATIONS

Klingbeil et al., Imaging and Analysis of the Fundus with Laser Scanners, Ophthalmologie 1982, pp. 275–277.

Primary Examiner—Rodney B. Bovernick
Assistant Examiner—P. M. Dzierzynski
Attorney, Agent, or Firm—Peter K. Kontler

[57] ABSTRACT

A microscope, whose ocular tubes receive light that is reflected by the blind spot or another selected portion in the innermost part of a human eye in response to illumination by a flash unit or a slit lamp, contains an ocular-like casing which replaces one of the oculars and contains a photodiode located in the respective image plane and generating signals denoting the intensity of light in the respective image plane. Such signals are transmitted to one input of a dividing circuit which further receives signals denoting the intensity of light which is emitted by the light source of the flash unit or slit lamp. The signal at the output of the dividing circuit is displaced and/or recorded and is indicative of reflectivity of the selected portion. The other ocular tube of the microscope contains a customary ocular with a marker located in the respective image plane.

12 Claims, 3 Drawing Figures

APPARATUS FOR EXAMINATION OF THE INNERMOST PART OF AN EYE

BACKGROUND OF THE INVENTION

The present invention relates to ophthalmological apparatus in general, and more particularly to improvements in ophthalmological apparatus which can be utilized for examination of the rear or innermost part of a human eye.

Conventional ophthalmological apparatus of the above outlined character include the slit lamp and the fundus camera. The slit lamp is used for visual examination of the rear or innermost part of the eye and actually constitutes a binocular microscope which is equipped with a light source. The microscope of a fundus camera comprises an attachment for a camera which renders it popssible to take photographs of the innermost part of the eye, e.g., of the region of the blind spot. It is further known to employ laser scanners as a means for facilitating diagnosing of the innermost part of the eye. Such apparatus comprise means for directing a collimated laser beam which is focussed, point-by-point, upon the innermost part of the eye. Reference may be had to pages 275–277 of the German-language publication entitled "Fortschrittliche Ophthalmologie" (Volume 79, 1982).

Heretofore known apparatus for the examination of the innermost part of the eye are capable of comparing different portions of the eye (e.g., different portions of the retina) in order to detect anomalies (if any). Such apparatus exhibit the drawback that they are not suited for quantitative detection and monitoring of long-range development of anomalous portions in the innermost part of the eye.

OBJECTS AND SUMMARY OF THE INVENTION

An object of the invention is to provide a novel and improved ophthalmological apparatus or instrument which is more versatile than the aforedescribed and other conventional apparatus.

Another object of the invention is to provide an apparatus which allows for quantitative determination of the absorptivity or reflectivity of selected portions of the eye and which is also suited for visual observation of such selected portions.

A further object of the invention is to provide an apparatus which is especially suited for the determination and monitoring of long-range development of anomalies in selected portions of the human eye.

Still another object of the invention is to provide an apparatus of the above outlined character which is not only simple and relatively inexpensive but is also capable of carrying out highly accurate measurements of absorptivity and/or reflectivity of selected portions of the eye, such as of the blind spot and/or of the area next to the blind spot.

An additional object of the invention is to provide an apparatus which can utilize certain conventional components in combination with novel and improved components which contribute to greater versatility and higher reliability of the apparatus.

Another object of the invention is to provide a novel and improved method of monitoring the innermost part of the eye.

A further object of the invention is to provide a novel and improved absorptivity and/or reflectivity measuring system for use in an apparatus of the above outlined character.

Another object of the invention is to provide a novel and improved slit lamp.

A further object of the invention is to provide a novel and improved fundus camera.

One feature of the invention resides in the provision of an ophthalmological instrument for examination of the innermost part of the human eye. The instrument comprises a microscope having at least one image plane, a light source which serves to illuminate a selected portion of the eye so that the illuminated portion is imaged in the image plane, and means for measuring the intensity of light which is reflected by the selected portion of the eye. The measuring means comprises a photosensitive element which is disposed in the one image plane and serves to transmit signals denoting the intensity of light which impinges thereon. The photosensitive element can include or constitute a photodiode, and the microscope can have two image planes and an ocular for observation of images in the other image plane.

The measuring means can further comprise a second photosensitive element which serves to transmit second signals denoting the intensity of light which is emitted by the light source, and means for processing the signals from the two photosensitive elements. Such processing means can comprise means for generating signals each of which is a quotient of signals which are generated by the two photosensitive elements. The light source can form part of a slit lamp or a flash unit.

The photosensitive element in the one image plane has a light-sensitive surface whose area is a fraction, preferably a small fraction, of the area of the one image plane. If the microscope has two image planes, it preferably further comprises a marker (e.g., a cross wires plate) disposed at a first location at least substantially at the center of the other image plane, and the light-sensitive surface of the photosensitive element is then disposed at a location in the one image plane which corresponds exactly to the location of the marker in the other image plane.

The instrument can further comprise adjustable diaphragm means disposed in the path of light which issues from the light source and having a preferably slit-shaped aperture whose size is adjustable to a minimum value at which the area of the image in the one image plane still exceeds the area of the light-sensitive surface.

The light source can constitute a source of polychromatic light and the spectral sensitivity range of the photosensitive element in the one image plane either conforms to or at least encompasses or embraces the spectral sensitivity range of the human eye.

The photosensitive element whose light-sensitive surface is or can be located in the one image plane is preferably installed in a casing which resembles an ocular and can be installed in the corresponding ocular tube of a binocular microscope. An adapter can be provided to facilitate removable mounting of the casing in the respective tube in a predetermined position so that the light-sensitive surface of the photosensitive element therein is located at a predetermined location in the one image plane. The ocular for the other image plane and the casing are installed in the rear end portions of the respective tubes, and the front end portions of such tubes receive the customary objective lenses.

The microscope can comprise a portion or extension which is connectable with a camera (such as a fundus camera). The instrument then further comprises suitable adapter means for separably securing the casing, with the respective photosensitive element therein, to the extension in lieu of the camera.

Another feature of the invention resides in the provision of a measuring apparatus which is or can be installed in an ophthalmological instrument of the type serving to render visible the innermost part of the human eye and having a housing with an optical axis, a first optical channel in the housing and an image plane in the channel. The measuring apparatus comprises a casing defining a second optical channel and having a second optical axis, adapter means arranged to connect the casing to the housing of the instrument so that the first and second optical axes coincide, a signal generating photosensitive element (preferably a photodiode) which is installed in the casing, which is located in the image plane when the adapter means connects the casing to the housing and which is held in a predetermined position (e.g., at or close to the center of the image plane) with reference to the housing as well as with reference to the adapter when the casing is properly attached to the housing, and means for evaluating and processing the signals which are generated by the photosensitive element when a selected portion of the innermost part of the eye is imaged into the image plane.

The housing of the instrument forms part or can form part of a microscope having two ocular tubes one of which defines the first optical channel and the other of which defines an additional optical channel. The casing preferably resembles an ocular, and the adapter means is arranged to separably secure the casing to the rear end portion of the one ocular tube, i.e., to that end portion which is remote from the light-receiving end of the one tube.

The housing of the ophthalmological instrument can be provided with a portion or extension for attachment of a camera (such as a fundus camera), and the adapter means can be arranged to connect the casing to the extension in lieu of the camera. The image plane which receives the light-sensitive surface of the photosensitive element is the image plane of the camera when the latter is attached to the extension in lieu of the casing.

The apparatus further comprises a light source (such as the light source of the aforementioned slit lamp or flash unit) which serves to illuminate a selected portion of the innermost part of the eye so that the selected portion is imaged in the image plane which is defined by the housing of the ophthalmological instrument and receives the light-sensitive surface of the photosensitive element. The evaluating and processing means then preferably includes a second photosensitive element which serves to generate signals denoting the intensity of light that issues from the light source and means for processing the signals from the two photosensitive elements. Such processing means can include a dividing circuit or other suitable means having discrete inputs for signals from the two photosensitive elements and an output for the transmission of signals corresponding to the quotients of signals from the two photosensitive elements. As mentioned above, the area of the light-sensitive surface of the photosensitive element in the casing is preferably a small fraction of the area of the respective image plane, and the spectral sensitivity range of such photosensitive element conforms to or encompasses the spectral sensitivity range of the human eye.

The novel features which are considered as characteristic of the invention are set forth in particular in the appended claims. The improved instrument itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
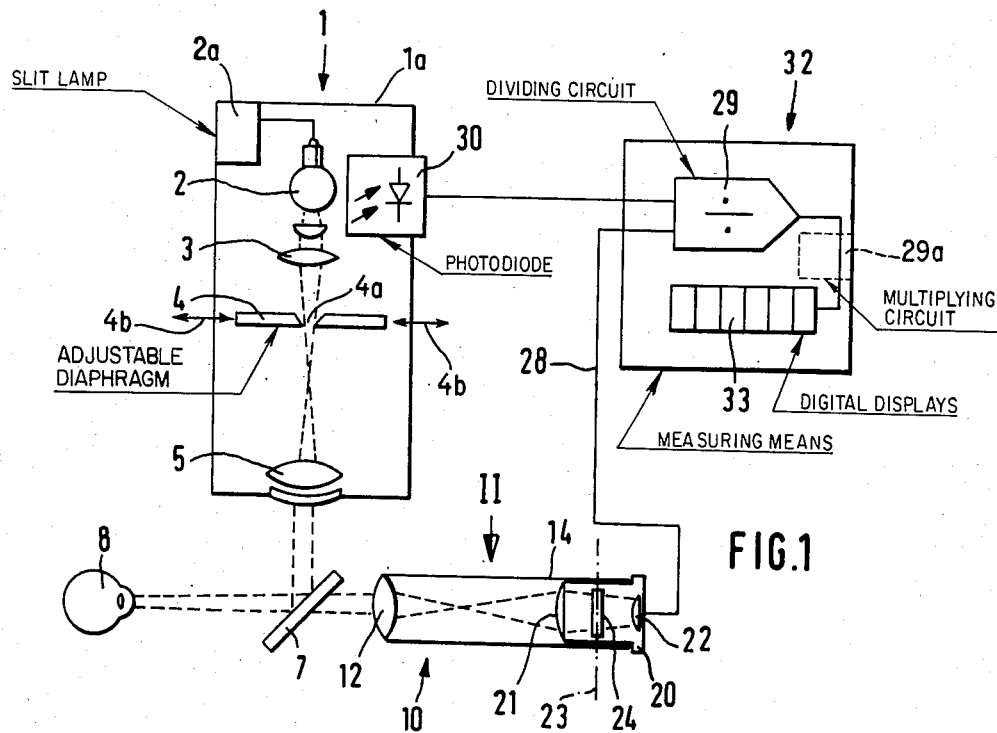
FIG. 1 is a schematic side elevational view of a binocular ophthalmological apparatus which includes a slit lamp and embodies one form of the present invention, the view being taken in the direction of arrow I in FIG. 2.
Figure 2:
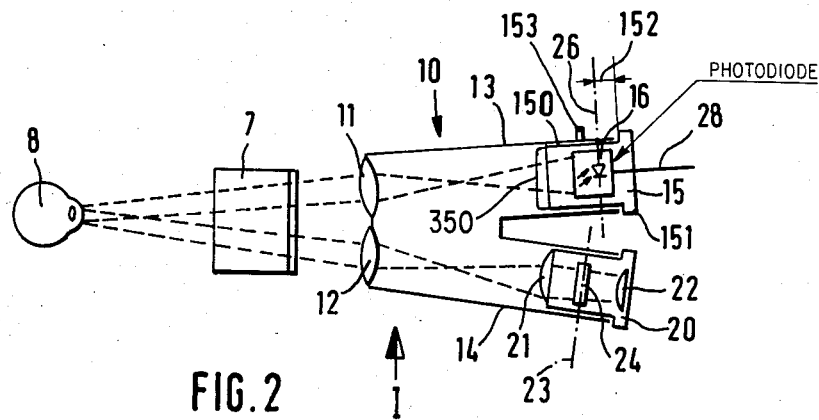
FIG. 2 is a plan view of a portion of the apparatus substantially as seen in the direction of arrow II in FIG. 1.

Referring first to FIGS. 1 and 2, there is shown an apparatus which comprises a suitable slit lamp 1 having a housing 1a for a light source 2 (e.g., an incandescent bulb or a halogen bulb), a collector lens 3 in front of the light source 2, an adjustable slit diaphragm (lamp field stop) 4 in front of the collector lens 3, and a condensor lens 5 in the exit opening of the housing 1a. The intensity of radiation which is emitted by the light source 2 can be adjusted by a suitable transformer 2a. The light beam which issues via condensor lens 5 impinges upon a semireflecting mirror 7 which reflects part of the light into a patient's eye 8 and causes the remaining part of light to enter a microscope 10. The reference character 4a denotes the slit-shaped aperture of the diaphragm 4, and the arrows 4b denote the directions in which the diaphragm 4 is adjustable to vary the size of the aperture 4a.

The microscope 10 is a binocular microscope with two objective lenses 11, 12 and a housing including two ocular tubes 13, 14. The common optical axis of the objective 11 and the optical channel defined by the ocular tube 13 makes an acute angle (e.g., an angle of 13 degrees) with the common optical axis of the objective 12 and the optical channel defined by the ocular tube 14. In the microscope of a conventional slit lamp type instrument, each of the ocular tubes contains an ocular or eyepiece. The two images which can be seen by looking through such eyepieces deviate slightly from one another and thus create a three-dimensional impression of the background or innermost part of the eye. In the illustrated apparatus, the ocular tube 13 does not contain an eyepiece; instead, this ocular tube contains an ocular-like casing 15 which is slipped into the rear end portion of the ocular tube 13 and contains a photodiode 16. The photodiode 16 forms part of a measuring apparatus 32 which will be described in detail hereinbelow. Due to its configuration resembling that of an ocular, the cylindrical external surface 150 of the casing 15 is slidable in the interior of the rear end portion of the tube 13 with a high degree of accuracy and comes to a halt when its annular flange-like stop 151 comes into abutment with the rear end face of the ocular tube 13. The internal surface of the ocular tube 13 is a cylindrical surface. The distance 152 between the plane of the photosensitive surface of the photodiode 16 and the plane of the front end face of the stop 151 is selected in such a way that, when the casing 15 is properly inserted into the ocular tube 13 of the housing of the microscope 10 so that the stop 151 engages its rear end face, the photodiode 16 is located in the image plane 26 of the tube 13.

The ocular tube 14 of the housing of the microscope 10 contains a microscope ocular or eyepiece 20 which, in the embodiment of FIGS. 1 and 2, is a huygens eyepiece wherein the real image is located between a field lens 21 and the eye lens 22. The image plane 23 (indicated by phantom lines) contains a marker in the form of a cross wires plate 24.

The light-sensitive surface of the photodiode 16 is disposed in the image plane 26 (indicated by phantom lines) so that the objective lens 11 images a selected portion of the innermost part of the eye 8 onto such light-sensitive surface. Due to the provision of the field lens 21, the distance between the image plane 23 and the objective lens 12 is somewhat less than the distance between the image plane 26 and the objective lens 11. The area of the light-sensitive surface of the diode 16 is smaller than the area which is imaged in the image plane 26 when the setting of the adjustable-slit diaphragm 4 is such that the size of its aperture 4a is reduced to a minimum. The position of the light-sensitive surface of the photodiode 16 in the image plane 26 corresponds exactly to the position of cross wires on the marker or plate 24 in the image plane 23. Since the images which are produced by the two objective lenses 11, 12 do not coincide, and since the cross wires on the plate 24 are located exactly at the center of the image plane 23, i.e., on the optical axis of the tube 14, the light-sensitive surface of the diode 16 is offset with reference to the center of the image plane 26 (i.e., with reference to the optical axis of the tube 13) to an extent which corresponds to the extent of divergence of the two images.

In order to ensure that the diode 16 assumes an optimum position when the casing 15 is fully inserted into the rear end portion of the tube 13, the casing 15 is preferably provided with a laterally extending pin-shaped projection 153 which is slidable in a complementary longitudinally extending slit of the tube 13. The projection 153 holds the casing 15 against angular movement with reference to the tube 13. The rear end portion of the tube 13 can be said to constitute an adapter which separably secures the casing 15 to the housing of the microscope 10 in such a way that the optical axes of the tube 13 and casing 15 coincide and the light-sensitive surface of the diode 16 is located in a predetermined portion of the image plane 26, i.e., in a predetermined position with reference to the tube 13 and its rear end portion or adapter.

The reference character 28 denotes conductor means connecting the diode 16 with one input of a signal processing and evaluating means here shown as a dividing circuit 29. As can be seen in FIG. 2, the conductor means 28 extends rearwardly from the casing 15. The other input of the dividing circuit 29 is connected with a photodiode 30 which is installed in the housing 1a of the slit lamp 1 and generates signals denoting the intensity of light issuing from the light source 2. The dividing circuit 29 forms part of the measuring means 32 and its output signal (i.e., a quotient of the signals received from the diodes 16 and 30) is transmitted to a digital display device 33 of the measuring means 32. The quotient of the aforementioned signals is indicative of the absorptivity or reflectivity of the tested portion in the innermost part of the eye 8, e.g., of the blind spot.

If desired, the measuring means 32 can further comprise a multiplying circuit 29a which multiplies the quotient signal from the output of the dividing circuit 29 with a constant, e.g., with a value which is selected in such a way that, when the apparatus is first put to use and the physician wishes to ascertain the absorptivity or reflectivity of the blind spot, the display device 33 indicates a value "100" if the examined eye is healthy.

As mentioned above, the light source 2 can constitute a conventional incandescent lamp which emits polychromatic light. In order to ensure that the information which is displayed by the device 33 invariably and unequivocally corresponds to the qualitatively estimatable absorptivity or reflectivity that can be gained as a result of visual examination, the diode 16 is selected in such a way that its spectral sensitivity range corresponds to the sensitivity range of the human eye or that it at least embraces or encompasses the spectral sensitivity range of the human eye.

A holder or support 350 for color filters can be provided at the front end of the casing 15. This enables the apparatus to measure the absorptivity of the rear part of the eye in different wavelength ranges.

The operation is as follows:

In the first step, the physician examines the innermost part of the eye 8 by looking through the ocular 20 in the ocular tube 14 of the housing of the microscope 10 while the innermost part of the eye is illuminated by the light source 2 of the slit lamp 1. If desired, the casing 15 can be extracted from the rear end portion of the tube 13 during such examination by way of the ocular 20 and is then replaced with a second ocular (e.g., an identical replica of the ocular 20) in order to obtain a three-dimensional effect. In order to ascertain the degree of absorptivity or reflectivity of the selected portion of the innermost part of the eye, e.g., of the blind spot, the casing 15 is reinserted into the rear end portion of the ocular tube 13 whereby the projection 153 slides in the slot of the tube 13 to ensure that the orientation of the casing 15 is satisfactory, i.e., that the diode 16 assumes the required position. The person in charge then moves the microscope 10 in the customary way (by resorting to mechanisms which are standard components for such purposes) so as to place the image of the blind spot or another selected portion of the eye 8 exactly at the intersection of the wires on the marker or plate 24 in the ocular 20. The value which is then indicated by the display device 33 is indicative of absorptivity of the selected portion in the innermost part of the eye 8.

The microscope 10 can be properly positioned so as to image a selected portion of the innermost part of the eye at a desired location even if the plate 24 with the crossed wire is omitted. To this end, the length and the width of the aperture 4a defined by the adjustable diaphragm 4 are adjusted with a high degree of accuracy so that the light source 2 of the slit lamp 1 illuminates only the selected portion (e.g., the blind spot) of the eye 8 or that the selected portion is located at the center of the illuminated part of the eye 8. Of course, a prerequisite for such mode of examination is that the photosensitive surface of the diode 16 be located on the axis of the bundle of light which enters the microscope 10 by way of the objective lens 11.

The improved measuring means 32 including the diodes 16, 30 can be utilized in a wide variety of ophthalmological instruments. All that is necessary is to conform the casing 15 and the system of photodiodes to the selected instrument. For example, if the slit lamp 1 is of the type which is equipped with ramsden eyepieces, it is merely necessary to employ a casing 15 which includes a longer tubular portion in order to ensure that the diode 16 will be located in the image plane. In a ramsden eyepiece, the image plane is located in front of the field lens.

If the apparatus is used in conjunction with a fundus camera and a binocular microscope, the photodiode 16 can be disposed in an eyepiece-like casing similar to the casing 15 of FIG. 2. However, it is equally possible to replace the fundus camera with a casing which contains the diode 16 and is mounted on a portion or extension of the microscope housing in lieu of the fundus camera. Moreover, it is also usable in a monocular microscope which is combined or combinable with a fundus camera.

Figure 3:
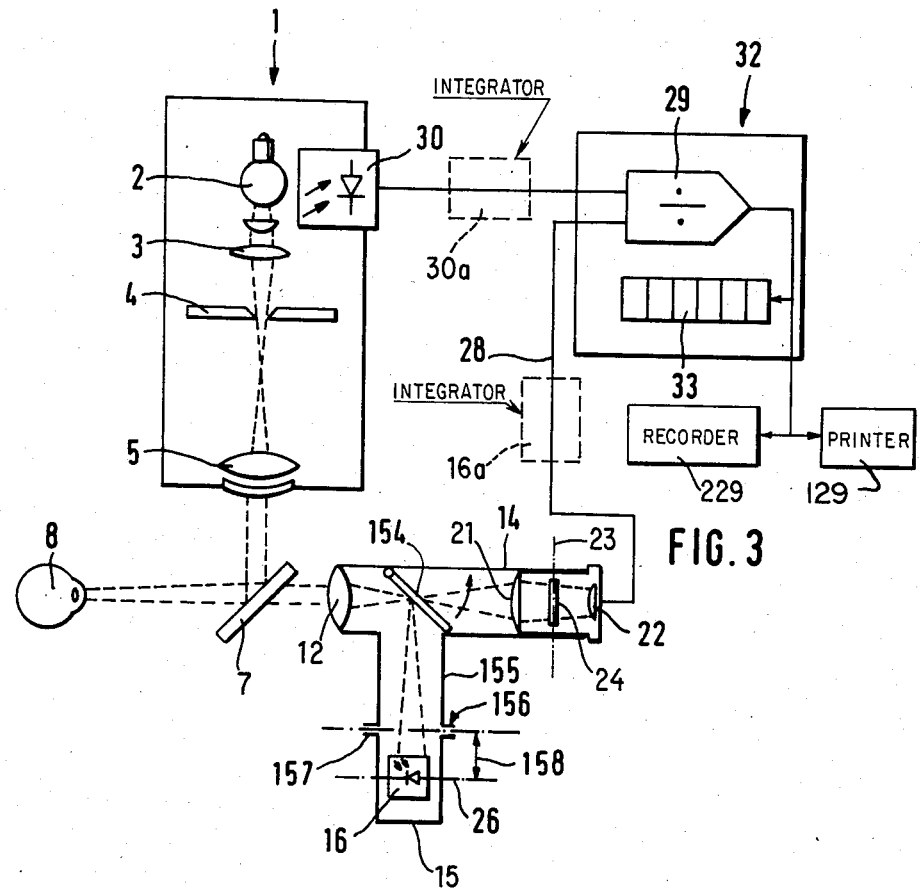
FIG. 3 is a schematic view similar to that of FIG. 1 but showing a monocular ophthalmological apparatus which can be coupled with a fundus camera.

FIG. 3 illustrates a monocular microscope with a fundus camera in a view corresponding to that of FIG. 1. For the sake of simplicity, all such parts which are identical with or clearly analogous to the corresponding parts of the apparatus of FIGS. 1 and 2 are denoted by similar reference characters. The ocular tube 14 contains a mirror 154 which is pivotable in a counterclockwise direction out of the path of radiation which propagates itself toward the eye lens 22. This renders it possible to observe the background of the eye 8 by looking through the eye lens 22. If the mirror 154 is thereupon pivoted to the position which is shown in FIG. 3, light which enters via objective lens 12 is reflected into a portion or extension 155 of the microscope housing which can be secured to a camera by means of an adapter including a bayonet lock or an analogous or equivalent quick-release connecting device. The bayonet lock or adapter has a first section 156 on the extension 155. The casing 15 which contains the photodiode 16 is provided with a second section 157 of the bayonet lock which is complementary to the bayonet lock section 156 on the extension 155 so that the casing 15 can be detachably coupled to the extension 155 in lieu of a fundus camera. The distance 158 between the diode 16 and the central plane of the bayonet lock 156, 157 is selected in such a way that, when the casing 15 is properly attached to the extension 155, the light-sensitive surface of the diode 16 is located in the image plane 26.

Since the image field of the camera is relatively large and, therefore, the density of light is relatively low, it is possible to carry out the measurement by resorting to the flash unit of the fundus camera, i.e., to the source of artificial light which is employed when the fundus camera is in actual use. The diode 30 is then installed in the housing of the flash unit. The measuring means 32 can comprise two integrators 16a, 30a which integrate the currents from the respective photodiodes 16 and 30 while the flash unit emits artificial light. The thus obtained integrated current signals are transmitted to the corresponding inputs of the dividing circuit 29 in the measuring means 32. In other words, the dividing circuit 29 transmits an output signal which is a quotient of the two integrated current signals.

In order to avoid inaccurate measurement due to irregular firing of the flash unit, it is advisable or desirable to place a hood of opal glass over the flash unit. Since a damaged or otherwise unhealthy eye is not supposed to be blinded by light issuing from a flash unit (this is not only unpleasant but can be quite damaging to the eye), it is normally preferred to carry out the examination with a light source which is used for normal examination of the eye, such as the aforedescribed light source 2 of the slit lamp 1.

The photodiode 30 could be omitted if the radiation issuing from the light source 2 is constant, e.g., if the connection between the light source 2 and the source (such as 2a in FIG. 1) of electrical energy for the light source contains a voltage regulator or the like which renders the diode 30 unnecessary because the light output of the source 2 is constant.

It is further possible to replace or equip the illustrated measuring means 32 with a suitable recording unit which records the information furnished by the output of the dividing circuit 29 or by the output of the multiplying circuit 29a. For example, and as shown schematically in FIG. 3, the output of the dividing circuit 29 can be connected with a printer 129 and a recorder 229. The device 129 can be used with or in lieu of the display device 33 and/or device 229. The same holds true for the other two devices 33 and 229. By continuously moving the microscope, the printing device 129 or the recorder 229 can record the progress of absorptivity along a line in the region of the innermost part of the eye.

An important advantage of the improved apparatus and its measuring means is that it enables a physician to select a preferred ophthalmological instrument of his or her choice which embodies the apparatus of the present invention for accurate and reliable determination of absorptivity of selected portions of the innermost part of the eye, such as the blind spot. By comparing the values which are obtained as a result of tests carried out at timely spaced intervals upon one and the same portion or group of portions of the innermost part of the eye, the physician can monitor the development and progress of diseases such as cerebral tumor or glaucoma. It has been found that the improved apparatus can indicate and/or record the degree of absorptivity or reflectivity of the blind spot (i.e., of the head of the optic nerve) with a high degree of accuracy and in a time-saving operation. Changes in the absorptivity or reflectivity of the blind spot are reliable indicators of the development and/or progress of the aforementioned diseases.

The slit lamp is available on the market and is manufactured and sold by Haag-Sheit AG, Lubefeld near Berne, Switzerland.

The fundus camera is available on the market and is manufactured and sold by Carl Zeiss AG, Oberkochen, Federal Republic Germany.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. In an ophthalmological instrument which is designed to render visible the innermost part of the human eye and has a microscope including a housing having a first optical axis and a first ocular tube defining a first optical channel and an image plane in said channel, the microscope further having a second ocular tube which defines an additional optical channel, a measuring apparatus comprising a casing resembling an ocular and defining a second optical channel and having a second optical axis; adapter means arranged to separably secure said casing to said first ocular tube so that the first and second optical axes coincide; a signal generating photosensitive element installed in said casing and located in said image plane when said adapter means connects said casing to said first ocular tube, said photosensitive element being held in a predetermined position with reference to said housing as well as with reference to said adapter means when the latter connects said casing to said first ocular tube; and means for evaluating the signals which are generated by said photosensitive element when a selected portion of the innermost part of the eye is imaged into said image plane.

2. The apparatus of claim 1, further comprising a light source arranged to illuminate a selected portion of the innermost part of the eye so that the selected portion is imaged in said image plane, said evaluating means including a second photosensitive element arranged to generate signals denoting the intensity of light which is emitted by said light source and means for processing the signals from said photosensitive elements.

3. The apparatus of claim 2, wherein said processing means comprises a circuit having inputs for the signals from said photosensitive elements and an output for transmission of signals corresponding to the quotients of signals from said photosensitive elements.

4. The apparatus of claim 1, wherein said photosensitive element has a photosensitive surface whose area is a small fraction of the area of said image plane.

5. The apparatus of claim 1, wherein the spectral sensitivity range of said photosentive element conforms to or encompasses the spectral sensitivity range of the human eye.

6. An ophthalmological instrument for examination of the innermost part of a human eye, comprising a microscope having two image planes; a light source arranged to illuminate a selected portion of the innermost part of the eye so that the illuminated portion is imaged in one of said planes; and means for measuring the intensity of light which is reflected by the selected portion of the innermost part of the eye, said measuring means including a photosensitive element which is disposed in said one image plane and is arranged to transmit signals denoting the intensity of light which impinges thereon, said photosensitive element having a light-sensitive surface and the area of such surface being a fraction of the area of said image plane, said microscope further having an ocular for the observation of images in the other of said image planes and a marker disposed at a location at least substantially at the center of said other image plane, the light-sensitive surface of said photosensitive element being disposed at a location of said one image plane which corresponds exactly to the location of said marker in said other image plane.

7. An ophthalmological instrument for examination of the innermost part of a human eye, comprising a microscope having at least one image plane; a light source arranged to illuminate a selected portion of the innermost part of the eye so that the illuminated portion is imaged in said plane; means for measuring the intensity of light which is reflected by the selected portion of the innermost part of the eye, said measuring means including a photosensitive element having a light-sensitive surface which is disposed substantially centrally of said image plane and said photosensitive element being arranged to transmit signals denoting the intensity of light which impinges thereon, the area of said light-sensitive surface being a fraction of the area of said image plane; and adjustable diaphragm means diposed in the path of light which is emitted by said light source and having an aperture whose size is adjustable to a minimum value at which the area of the image in said image plane still exceeds the area of said light-sensitive surface.

8. The instrument of claim 7, wherein said diaphragm has a slit-shaped aperture.

9. An ophthalmological instrument for examination of the innermost part of a human eye, comprising a microscope having two ocular tubes and two image planes, one in each of said tubes; a light source arranged to illuminate a selected portion of the innermost part of the eye so that the illuminated portion is imaged in one of said planes; and means for measuring the intensity of light which is reflected by the selected portion of the innermost part of the eye, said measuring means including a photosensitive element which is disposed in said one image plane and is arranged to transmit signals denoting the intensity of light which impinges thereon, said microscope further comprising an ocular in the tube for the other of said image planes and a casing removably installed in the tube for said one image plane, said element being installed in said casing.

10. The instrument of claim 9, wherein each of said tubes has a light-receiving front end portion and a rear end portion, said ocular and said casing being disposed in the rear end portions of the respective tubes.

11. The instrument of claim 10, wherein said casing resembles an ocular.

12. In an ophthalmological instrument which is designed to render visible the innermost part of the human eye and has a housing having a first optical axis and defining a first optical channel and an image plane in said channel, the housing having an extension for attachment of a camera, a measuring apparatus comprising a casing defining a second optical channel and having a second optical axis; adapter means arranged to connect said casing to said extension in lieu of the camera so that the first and second optical axes coincide, said image plane being the image plane of the camera when the latter is attached to said extension in lieu of said casing; a signal generating photosensitive element installed in said casing and located in said image plane when said adapter means connects said casing to said extension, said photosensitive element being held in a predetermined position with reference to said housing as well as with reference to said adapter means when the latter connects said casing to said extension; and means for evaluating the signals which are generated by said photosensitive element when a selected portion of the innermost part of the eye is imaged into said image plane.

* * * * *